Figure 1:
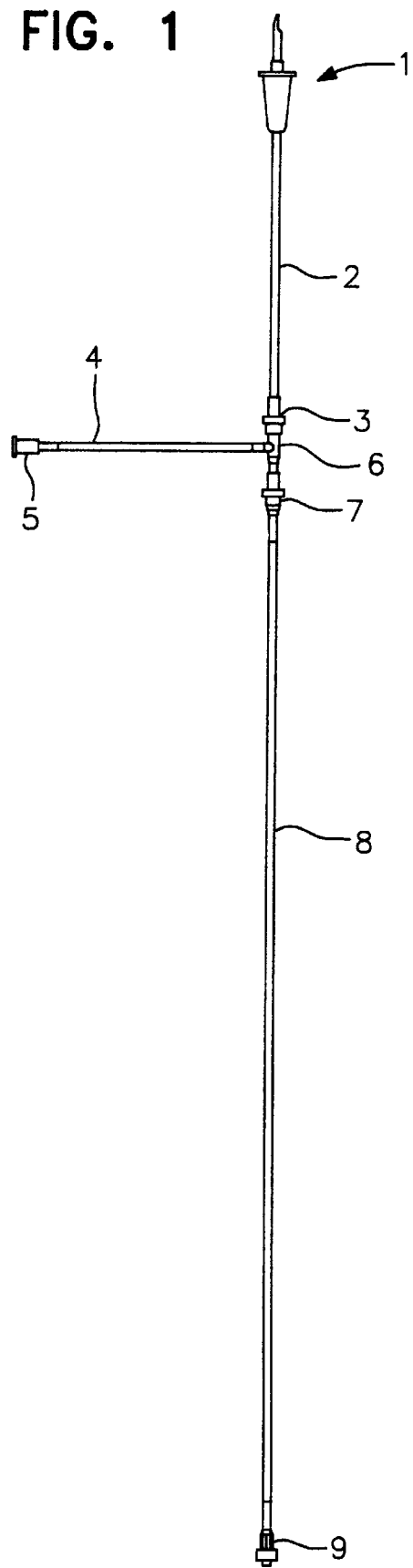

United States Patent [19]
Wijnhoud

[11] Patent Number: 6,102,889
[45] Date of Patent: Aug. 15, 2000

[54] STERILE SOLUTION INFUSION APPARATUS

[75] Inventor: Pieter Robert Wijnhoud, Auckland, New Zealand

[73] Assignee: REM Systems Limited, Auckland, New Zealand

[21] Appl. No.: 09/086,624

[22] Filed: May 29, 1998

[30] Foreign Application Priority Data

Oct. 23, 1997 [NZ] New Zealand .......................... 329024

[51] Int. Cl.[7] .................................................. A61M 5/14
[52] U.S. Cl. .............................................. 604/80; 604/81
[58] Field of Search ............................... 604/80, 81, 264, 604/284, 30–34, 246–248, 523

[56] References Cited

U.S. PATENT DOCUMENTS 5,935,100  8/1999  Myers ........................................ 604/81
5,961,488  10/1999  Barak ........................................ 604/80

*Primary Examiner*—John D. Yasko
*Attorney, Agent, or Firm*—Jacobson, Price, Holman & Stern, PLLC

[57] ABSTRACT

A sterile solution infusion apparatus having a first line to intake infusion liquid and transport it via two anti-syphon one way valves to an output end and having a branch intake line to the first line between the anti-syphon one way valves to allow the input under pressure of a different infusion feed.

12 Claims, 2 Drawing Sheets

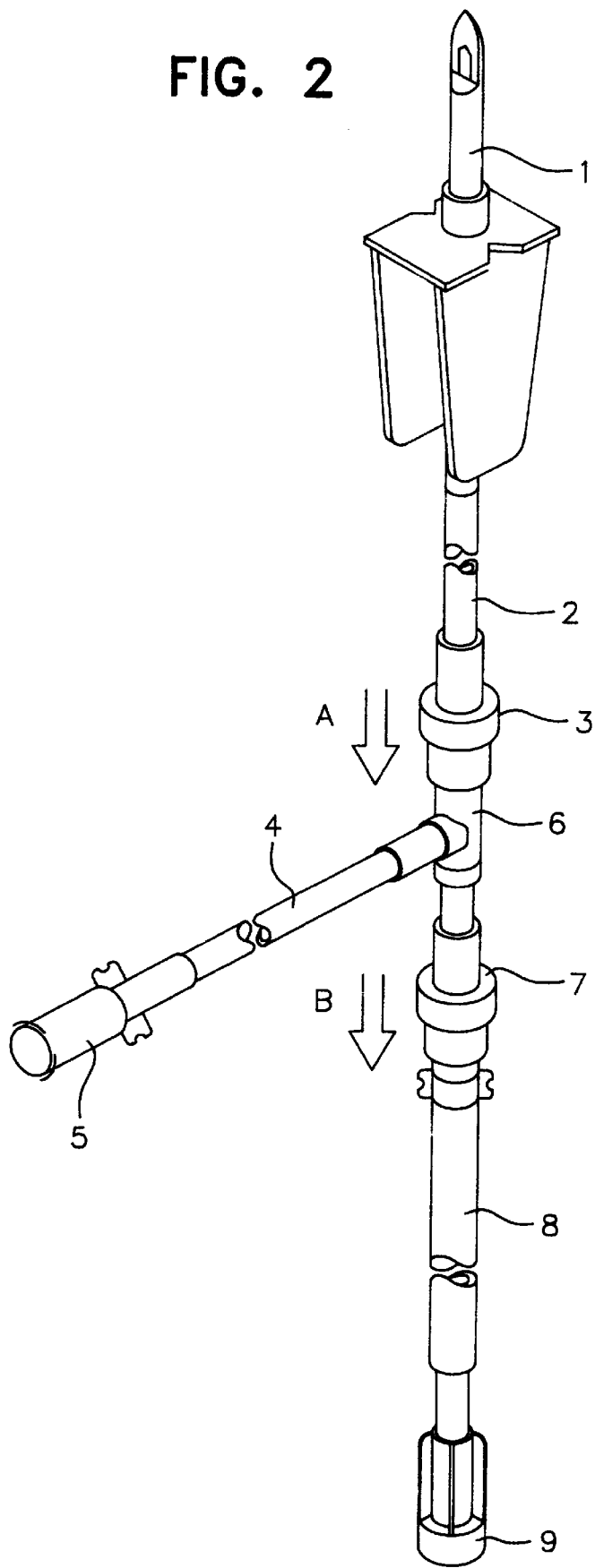

STERILE SOLUTION INFUSION APPARATUS

The present invention relates to apparatus suitable for use during sterile solution infusion (e.g.; epidural, intravenous, and enteral) related methods and kits involving such apparatus whether alone or in conjunction with other apparatus, e.g.; syringes etc.

In a first aspect the present invention consists in apparatus suitable for use during sterile solution infusion, said apparatus comprising or including intake means for an infusion-liquid (e.g.; a spike able to penetrate a reservoir of an infusion liquid and to take a feed of liquid therefrom), a conduit (the "first conduit") from said intake means, a first (preferably anti-syphon) one way valve to take infusion liquid from said first conduit, a T-connector to take infusion liquid from said first (preferably anti-syphon) one way valve, a second (preferably anti-syphon) one way valve to take infusion liquid from said T-connector, a conduit (the "second conduit") to take liquid from said second (preferably anti-syphon) one way valve, an output connector at an end of said second conduit, a conduit (the "third conduit") to take liquid from said T-connector without passing through said second (preferably anti-syphon) one way valve and/or to provide liquid into said T-connector between said anti-syphon one way valves, and a connector to said third conduit.

Preferably the apparatus is for epidural, intravenous or enteral infusion.

Preferably at least one (and preferably both) one way valves is an anti-syphon one way valve connector.

Preferably the connector of said third conduit allows association with means to effect pressure variation in said third conduit (e.g.; a hypodermic syringe).

Preferably at least one preferably all of said conduits are flexible.

Preferably said output connector is of a male type.

Preferably said connector enables association with, for example, a catheter.

Preferably said second conduit is longer than said third conduit and preferably also said first conduit.

Preferably said intake means is a non vented spike.

In a further aspect the present invention consists in, as part of a kit, apparatus as previously defined and/or as hereinafter exemplified.

In a further aspect the present invention consists in a method of ducting a sterile solution infusion liquid which comprises, using apparatus of the present invention, engaging the intake means into or to a source of infusion liquid, engaging said output connector to a feed line into a patient, and controlling the feed of liquid to the patient by inducing a pumping effect via the connector of said third conduit.

Preferably such infusion is epidural, intravenous or enteral.

As used herein "T-connector" may include any multi ported type connector provided it (or any equivalent assembly) allows for connection of at least three conduits, the third conduit being between two anti-syphon one way valves.

Any reference to direct connection of a said one way valve to said T-connector is of a preference only.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Preferred forms of the present invention will now be described with reference to the accompanying drawings in which;

FIG. 1 is a diagram showing the preferred apparatus of the present invention, and FIG. 2 is a view of the same apparatus as FIG. 1 but showing with the arrows "A" and "B" the one way direction of the respective anti-syphon one way valves preferably directly connected to the T-connector.

In the preferred form of the present invention the apparatus comprises the following;

1) Spike (non-vented) (intake means)
2) Standard bore IV Tubing (50 cm) (first conduit)
3) Anti-syphon one way valve (first anti-syphon one way valve)
4) Non-Kink IV Tubing with yellow identification stripe (30 cm) (third conduit)
5) Female Luer Lock Connector (the connector to said third conduit)
6) T-Connector
7) Anti-syphon one way valve (second anti-syphon one way valve)
8) Non-Kink IV Tubing with yellow identification stripe (200 cm) (second conduit)
9) Male Luer-lock Connector (yellow) (output connector)

Persons skilled in the art will appreciate how the provision of the side arm provided by the third conduit positioned between the two anti-syphon valves from the T-connector provides for infusion control.

Whilst we have referred herein throughout specifically to a T-connector any three way connector such as a "Y" site or similar could be used. Indeed, if desired, a multiple connector greater than a three way connector could be utilised should there be some reason for other inputs into the system.

An important facet of the invention is that the junction provided is positioned between the two anti-syphon one way valves and the direction of allowed liquid flow is in the direction of arrows "A" and "B" shown in FIG. 2.

In use therefore the connector 9 can be engaged to a catheter (feed line) into a patient and the infusion liquid taken down in from the spike or intake means 1. As it is however even if no additional liquid is to be introduced via the connector 5, the connector 5 connected via the third conduit between the two anti-syphon one way valves serves a control function. Whilst simple one way valves would permit solution to flow directly to a patient out of the connector 9, the anti-syphon valves require a positive or negative pressure in order to function as a pump from the first anti-syphon one way valve down into the second anti-syphon one way valve thereby ensuring that a physician, anaesthetist or the like can control the movement of pressurised liquid down through the anti-syphon one way valve 7 by manipulating pressures within the branch line.

It is believed that apparatus in accordance with the present invention will find widespread usage.

What is claimed is:

1. Apparatus suitable for use during sterile solution infusion, said apparatus comprising a single intake means for connection to a single container of infusion liquid, a first conduit connected to said single intake means, a first one way valve connected to said first conduit to infusion liquid under pressure from said first conduit, an at least three way connector, a first arm of said at least three way connector being connected to said first one way valve to transfer the infusion liquid from said first anti-syphon one way valve, a second one way valve connected to a second arm of said at least three way connector to transfer the infusion liquid from said first arm of said at least three way connector, a second conduit connected to said second one way valve to transfer the liquid from said second one way valve, an output connector at an end of said second conduit, a third conduit connected to a third arm of said at least three way connector for removal of infusion liquid from said first arm of said at least three way connector and for inputting liquid to said second arm of said at least three way connector and through said second one way valve while passage of input liquid from said third conduit is prevented from passing through said first one-way valve due to an orientation of said first one way valve which only allows passage of liquid in a direction from said first conduit towards at least one of said second conduit and said third conduit, and a connector at an end of said third conduit.

2. Apparatus of claim 1 wherein said first one way valve is an anti-syphon valve.

3. Apparatus of claim 1 or 2 wherein said second one way valve is an anti-syphon valve.

4. Apparatus of claim 1, wherein said single intake means is a member able to penetrate a single reservoir of an infusion liquid and to take a feed of liquid therefrom.

5. Apparatus for any one of the preceding claims when for epidural, intravenous or enteral infusion.

6. Apparatus of any one of the preceding claims wherein the connector of said third conduit allows association with means to effect pressure variation in said third conduit.

7. Apparatus of claim 6 wherein said means to effect pressure variation is a hypodermic syringe.

8. Apparatus of any one of the preceding claims wherein said conduits are flexible.

9. Apparatus of claim 1, wherein said output connector at the end of the second conduit is of a male type.

10. Apparatus of claim 1, wherein said output connector at the end of the second conduit enables association with a catheter.

11. Apparatus of any one of the preceding claims wherein said second conduit is longer than said third conduit and also said first conduit.

12. Apparatus of claim 4 wherein said single intake means is a non vented spike.

* * * * *